| United States Patent [19] | [11] Patent Number: 4,950,832 |
|---|---|
| Kojima | [45] Date of Patent: Aug. 21, 1990 |

[54] METHOD FOR PREPARATION OF DIALKYLNAPHTHALENES AND CATALYST FOR THE SAME

[75] Inventor: Mitsuo Kojima, Yokohama, Japan

[73] Assignee: Nikki Chemical Co., Ltd., Tokyo, Japan

[21] Appl. No.: 221,304

[22] Filed: Jul. 19, 1988

[30] Foreign Application Priority Data

Jul. 29, 1987 [JP] Japan .................................. 62-187682

[51] Int. Cl.$^5$ ................................................ C07C 2/70
[52] U.S. Cl. ..................................... 585/463; 585/462
[58] Field of Search ................................ 585/462, 463

[56] References Cited

U.S. PATENT DOCUMENTS

| 2,584,103 | 2/1952 | Pines et al. | 585/463 |
|---|---|---|---|
| 3,083,243 | 3/1963 | Carden | 585/510 |
| 3,200,163 | 8/1965 | Fenske | 585/463 |
| 3,248,442 | 4/1966 | Goble et al. | 585/463 |
| 3,417,148 | 12/1968 | Fishel | 585/463 |
| 3,437,702 | 4/1967 | Kirk, Jr. et al. | 585/462 |
| 4,032,474 | 6/1977 | Goudriaan et al. | 502/228 |
| 4,038,213 | 7/1977 | McClure et al. | 502/159 |
| 4,220,557 | 9/1980 | Mickelson | 502/228 |
| 4,530,756 | 7/1985 | Chang et al. | 585/463 |

FOREIGN PATENT DOCUMENTS

| 17-3617 | 2/1942 | Japan . |
|---|---|---|
| 56-2532 | 1/1981 | Japan . |
| 1579473 | 10/1977 | United Kingdom . |
| 2104795 | 3/1983 | United Kingdom . |

*Primary Examiner*—Patrick P. Garvin
*Assistant Examiner*—E. D. Irzinski
*Attorney, Agent, or Firm*—Cushman, Darby & Cushman

[57] ABSTRACT

Dialkylnaphthalenes, especially 2,6-dialkylnaphthalene can be prepared with good yield for a long time by reacting naphthalene and/or monoalkylnaphthalenes with $C_2$–$C_4$ olefin in the presence of silica-alumina catalyst containing 0.1–15 weight percent of fluorine under suitable conditions.

4 Claims, No Drawings

METHOD FOR PREPARATION OF DIALKYLNAPHTHALENES AND CATALYST FOR THE SAME

BACKGROUND OF THE INVENTION

1. Field of the Invention

The present invention relates to a method for preparation of dialkylnaphthalenes, especially 2,6-dialkylnaphthalene and a catalyst for the use.

2. Description of the Prior Art

In Japanese patent publication Tokkosho No. 56-2532, there has been proposed a method for preparation of beta-isopropylnaphthalene comprising: reacting naphthalene with propylene in the presence of a solid acidic catalyst such as silica, alumina or zeolite, subsequently collecting diisopropylnaphthalene fraction by distillation, separating 2,6-diisopropylnaphthalene from the fraction by crystallization and forming beta-isopropylnaphthalene by transalkylation between naphthalene and 2,6-diisopropylnaphthalene. But such solid acidic catalyst is not satisfactory from the viewpoint of transalkylation activity, isomerization activity and lifetime of the catalyst in the preparation of dialkylnaphthalenes. (cf. Comparative Examples 1, 3, 4, 8, 9 and 10 described below)

In Japanese patent publication Tokkosho 42-3617, there has been proposed a method of olefin-alkylation of an aromatic hydrocarbon at 1-200 atm. and 210°-325° C. in the presence of a catalyst composed of a fire-proof inorganic oxide selected from a group of alumina, silica, silica-alumina, silica-alumina-magnesia, silica-magnesia, silica-zirconia, alumina-zirconia, alumina-boria, zirconium dioxide and titanium dioxide, which contains 2-12 weight percent, preferably 2-8 weight percent of fluorine, with Hammett's reaction constant of −8.0 or less and is calcined at 450°-700° C. in an inert gas substantially free of water and oxygen, and a method of transalkylation of the alkylaromatic hydrocarbon at 1-200 atm. and 220°-350° C. Alkylation and transalkylation of single-ring aromatic hydrocarbons only were described as examples, but naphthalene and alkylnaphthalenes were referred as aromatic hydrocarbons therein.

However, neither all of above-mentioned inorganic oxides containing fluorine are always suitable as the catalyst for preparation of dialkylnaphthalenes by alkylation of naphthalene and/or a monoalkylnaphthalene with an olefin (cf. Comparative Examples 5, 6 and 7 described below), nor suitable reaction conditions for the preparation of dialkylnaphthalenes were mentioned in it.

SUMMARY OF THE INVENTION

It is an object of the present invention to provide a method for preparation of dialkylnaphthalenes, more particularly for the preparation of 2,6-dialkylnaphthalene with high yield for a long term.

DETAILED DESCRIPTION OF THE PREFERRED EMBODIMENTS

The present invention is a method for preparation of dialkylnaphthalenes comprising: reacting naphthalene and/or monoalkylnaphthalenes having an alkyl group of 1 to 4 carbon atom(s) with an olefin having 2 to 4 carbon atoms, in the presence of a silica-alumina catalyst containing 0.1-15 weight percent of fluorine, under conditions of molar ratio of the olefin to the naphthalene and/or the monoalkylnaphthalenes of 0.1-10, a reaction temperature of 200°-450° C., a reaction pressure of 2-30 kg/cm$^2$G and a LHSV (Liquid Hourly Space Velocity) of 0.2-10 Hr$^{-1}$.

The silica-alumina as a base of the catalyst to be used in the present invention may contain 10-80 weight percent of $Al_2O_3$. Commercial silica-alumina catalyst can be used. Fluorine content of the catalyst should be within 0.1-15 weight percent, preferably 0.5-13 weight percent. Because fluorine content of less than 0.1 weight percent gives lower treating effect of fluorine and fluorine content of more than 15 weight percent brings about the destruction of silica-alumina crystal structure by the formation of $AlF_3$.

As the fluorinating agent of the silica-alumina, fluorine-containing compounds such as ammonium fluorine, hydrogen fluoride, methyl ammonium fluorine, a metal-fluoride or a fluorocarbon may be used. If the fluorinating agent is a liquid or a solution, conventional dipping method may be applied. If the fluorinating agent is a solid, the fluorinating agent and the silica-alumina may be pulverized together, blended and mechanically molded. If the fluorinating agent is a gas, it will be introduced into the silica-alumina layer under heating at 300°-600° C. for fluorination.

Raw material to be subjected to alkylation may be naphthalene or monoalkylnaphthalenes having an alkyl group of 1 to 4 carbon atom(s) or a mixture of them. They may contain further di-, tri- or tetra-alkylnaphthalenes therein.

In order to raise the total yield of dialkylnaphthalene, especially 2,6-dialkylnaphthalene, it is preferable to recycle a mixture of naphthalene, mono-, di-, tri-, and tetra-alkylnaphthalenes obtained after separation of desired dialkylnaphthalene(s) from the reaction products to aforementioned reaction process and subjected to the reaction according to the present invention.

The separation of desired dialkylnaphthalene(s) from the reaction products can be conducted by distillation, crystallization or adsorption method.

An olefin having 2 to 4 of carbon atoms, preferably propylene is used as the alkylating agent.

The molar ratio of the olefin to the naphthalene and/or monoalkylnaphthalenes should be 0.1-10, preferably 0.3-5, and more preferably 0.5-3.

The reaction temperature should be 200°-450° C. preferably 220°-350° C., because too low temperature brings about incomplete transalkylation and results in low yield of dialkylnaphthalenes, especially 2,6-dialkylnaphthalene. On the contrary, too high temperature brings about dealkylation together with the alkylation and tends to induce the polymerization of reactants.

The reaction pressure should be 2-30 kg/cm$^2$G, preferably 3- 15 kg/cm$^2$G. The LHSV should be 0.2-10 Hr$^{-1}$, preferably 0.2-5 Hr$^{-1}$.

The present invention is explained in detail in following Examples.

EXAMPLE 1

10 cc of silica-alumina ($Al_2O_3$: 28 weight percent) pulverized and regulated to 12-28 mesh particles were passed through with decalin containing 2000 volume ppm of 1-fluorohexane for 24 hours at 400° C., 10 kg/cm$^2$G and LHSV 1.0 Hr$^{-1}$. Then, they were calcined in air flow for 3 hours at 530° C., and a silica-alumina catalyst containing 0.6 weight percent of fluorine was obtained.

6 cc of the said fluorine-containing catalyst were filled into a small size catalyst activity tester, to where naphthalene and two-fold molar quantity of propylene to the naphthalene were supplied for alkylation under conditions of 280° C., 7.0 kg/cm²G and LHSV 1.0 Hr$^{-1}$.

COMPARATIVE EXAMPLE 1

The silica-alumina used in Example 1 without the fluorine-treating was used as the catalyst and the alkylation was carried out under the same conditions as in Example 1.

Test results of the alkylations of Example 1 and Comparative Example 1 are shown in TABLE 1.

TABLE 1

| Lapse of time | Example 1 Yield (molar %) | | Comparative Example 1 Yield (molar %) | |
|---|---|---|---|---|
| | *1 DIPN | *2 2,6-DIPN | *1 DIPN | *2 2,6-DIPN |
| Initial time | 55.6 | 21.7 | 54.8 | 20.6 |
| 200 hours | 55.5 | 21.4 | 53.2 | 19.7 |
| 600 hours | 51.3 | 19.6 | 45.8 | 15.6 |

*1: diisopropylnaphthalenes containing 2,6-diisopropylnaphthalene
*2: 2,6-diisopropylnaphthalene.

By using the silica-alumina catalyst containing 0.6 weight percent of fluorine, the yield of diisopropylnaphthalenes, especially of 2,6-diisopropylnaphthalene was improved and the life of catalyst was prolonged.

EXAMPLES 2 TO 8 AND COMPARATIVE EXAMPLE 2

100 grams of the same type of silica-alumina used in Example 1 were impregnated with 70 cc of 10% aqueous solution of HF. Then, they were dried at 120° C. for 24 hours, and were calcined in air-atmosphere at 530° C. for 3 hours. The composition of thus prepared Catalyst 1 was silica-alumina containing 4.3 weight percent of fluorine [described as F(4.3)SiO$_2$·Al$_2$O$_3$ in TABLE 2].

In the same way as of Catalyst 1, were prepared Catalyst 2 with a composition of F(2.1)SiO$_2$·Al$_2$O$_3$ [silica-alumina catalyst containing 2.1 weight percent of fluorine] and Catalyst 3 with a composition of F(1.0)SiO$_2$·Al$_2$O$_3$ [silica-alumina catalyst containing 2.1 weight percent of fluorine].

100 grams of the same type of silica-alumina used in Example 1 were impregnated with 80 cc of distilled water solution dissolved 7 grams of NH$_4$F. Then, they were dried at 120° C. for 24 hours, and were calcined in air-atmosphere at 530° C. for 3 hours. The composition of thus prepared Catalyst 4 was F(1.6)SiO$_2$·Al$_2$O$_3$ [silica-alumina catalyst containing 1.6 weight percent of fluorine].

In the same way as above, were prepared Catalyst 5 with the composition of F(12.6)SiO$_2$·Al$_2$O$_3$ [silica-alumina catalyst containing 12.6 weight percent of fluorine] and Catalyst 6 with the composition of F(16)SiO$_2$·Al$_2$O$_3$ [silica-alumina catalyst containing 16 weight percent of fluorine]. The Catalyst 6 was outside the range of this invention because it contained 16 weight percent of fluorine.

Above-mentioned Catalysts 1 to 6 were filled into a small size catalyst activity tester one by one and were subjected to the same reaction test one after another as Example 1, except changing the LHSV and the reaction temperature. The test results are shown in TABLE 2.

TABLE 2

| | Ex. 2 | Ex. 3 | Ex. 4 | Ex. 5 | Ex. 6 | Ex. 7 | Ex. 8 | Comp. Ex. 2 |
|---|---|---|---|---|---|---|---|---|
| Catalyst | Cat. 1 | Cat. 2 | Cat. 3 | Cat. 4 | Cat. 5 | Cat. 1 | Cat. 2 | Cat. 6 |
| | F (4.3) | F (2.1) | F (1.0) | F (1.6) | F (12.6) | F (4.3) | F (2.1) | F (16) |
| | SiO$_2$·Al$_2$O$_3$ | SiO$_2$·Al$_2$O$_3$ | SiO$_2$·Al$_2$O$_3$ | SiO$_2$·Al$_2$O$_3$ | SiO$_2$·Al$_2$O$_3$ | SiO$_2$·Al$_2$O$_3$ | SiO$_2$·Al$_2$O$_3$ | SiO$_2$·Al$_2$O$_3$ |
| Conditions | | | | | | | | |
| LHSV (Hr$^{-1}$) | 1.0 | 4.8 | 2.4 | 1.0 | 1.0 | 9.6 | 1.0 | 4.8 |
| Temp. (°C.) | 230 | 280 | 255 | 235 | 255 | 280 | 205 | 280 |
| Pressure | 7.0 | 7.0 | 7.0 | 7.0 | 7.0 | 7.0 | 7.0 | 7.0 |
| Results (molar %) | | | | | | | | |
| naphthalene | 4.0 | 2.2 | 2.6 | 3.8 | 1.4 | 5.9 | 6.1 | 3.4 |
| MIPN | 19.4 | 19.2 | 21.0 | 19.8 | 16.1 | 21.2 | 17.6 | 15.3 |
| DIPN | 49.7 | 54.0 | 49.6 | 51.1 | 54.5 | 46.9 | 46.2 | 44.6 |
| (2,6DIPN) | (19.5) | (20.8) | (18.9) | (20.1) | (21.5) | (17.6) | (17.1) | (15.2) |
| TIPN | 24.4 | 22.8 | 24.4 | 22.8 | 24.4 | 23.9 | 26.9 | 32.7 |
| TetraIPN | 2.5 | 2.0 | 2.2 | 2.5 | 3.5 | 2.1 | 3.2 | 3.9 |

Pressure: (kg/cm² G)
MIPN: monoisopropylnaphthalenes.
DIPN: diisopropylnaphthalenes containing 2,6-diisopropylnaphthalene
(2,6DIPN): 2,6-diisopropylnaphthalene
TIPN: triisopropylnaphthalenes
TetraIPN: tetraisopropylnaphthalenes As is shown in TABLE 2, the yield of diisopropylnaphthalenes, especially 2,6-diisopropylnaphthalene was low in Comparative Example 2 using the Catalyst 6 containing 16 weight percent of fluorine.

COMPARATIVE EXAMPLES 3-7

In Comparative Examples 3 & 4, were used the same type of silica-alumina catalyst as used in Comparative Example 1.

In Comparative Example 5, was used an alumina catalyst containing 2.3 weight percent of fluorine [described as F(2.3)Al$_2$O$_3$ in TABLE 3] which was prepared as follows: 85 grams of commercial alumina catalyst particles were impregnated with an aqueous solution of alumina fluoride (NH$_4$F 8.4 grams+pure water 75 grams) then dried at 120° C. for 24 hours and calcinated in air atomsphere at 530° C. for 3 hours.

In Comparative Example 6, was used a silica-titania (TiO$_2$: 90 wt. %) catalyst containing 3.1 weight percent of fluorine [described as F(3.1)SiO$_2$·TiO$_2$ in TABLE 3], prepared by the same process as above.

In Comparative Example 7, was used an alumina-boria (B$_2$O$_3$: 20 weight percent) catalyst containing 2.6 weight percent of fluorine [described as F(2.6)Al$_2$O$_3$·B$_2$O$_3$ in TABLE 3] prepared by the same way as above.

Test results evaluated by the same way as in Example 1, except changing LHSV and reaction temperature are shown in TABLE 3.

TABLE 3

|  | Comp. Ex. 3 | Comp. Ex. 4 | Comp. Ex. 5 | Comp. Ex. 6 | Comp. Ex. 7 |
|---|---|---|---|---|---|
| Catalyst | $SiO_2.Al_2O_3$ | $SiO_2.Al_2O_3$ | F (2.3) $Al_2O_3$ | F (3.1) $SiO_2.TiO_2$ | F (2.6) $Al_2O_3.B_2O_3$ |
| Conditions |  |  |  |  |  |
| LHSV ($Hr^{-1}$) | 1.0 | 4.8 | 1.0 | 1.2 | 1.2 |
| Temp. (°C.) | 235 | 285 | 280 | 280 | 280 |
| Pressure | 7.0 | 7.0 | 7.0 | 6.5 | 6.5 |
| Results (molar %) |  |  |  |  |  |
| Naphthalene | 4.4 | 5.9 | 12.8 | 12.5 | 1.7 |
| MIPN | 19.1 | 19.8 | 17.6 | 16.9 | 13.5 |
| DIPN | 46.4 | 43.1 | 30.1 | 37.3 | 45.8 |
| (2,6DIPN) | (16.9) | (14.7) | (6.0) | (9.5) | (14.9) |
| TIPN | 27.2 | 28.3 | 30.8 | 30.5 | 36.0 |
| TetraIPN | 2.6 | 2.9 | 8.7 | 2.6 | 3.0 |

MIPN: monoisopropylnaphthalenes.
DIPN: diisopropylnaphthalenes containing 2,6-diisopropylnaphthalene
(2,6DIPN); 2,6-diisopropylnaphthalene
TIPN: triisopropylnaphthalenes
TetraIPN: tetraisopropylnaphthalenes As is shown in TABLE 3, yields of diisopropylnaphthalenes, especially 2,6-diisopropylnaphthalene in each Comparative Examples were low.

It is apparent that the same type of the alumina catalyst containing fluorine used for alkylation of benzene in an example of aforementioned Tokkosho 42-3617 was much inferior for the dialkylation, especially 2,6-dialkylation of naphthalene (cf. Comparative Example 5) and the alumina-boria catalyst described in Tokkosho 42-3617 showed the same tendency too (Comparative Example 7).

EXAMPLE 9

Alkylation of beta-isopropylnaphthalene with propylene was carried out using the Catalyst 1 (silica-alumina catalyst containing 4.3 weight percent of fluorine) in the same manner as Example 1 under conditions described in TABLE 4.

COMPARATIVE EXAMPLE 8

The silica-alumina used in Example 9 without the fluorine-treating was used as the catalyst and the alkylation of beta-isopropylnaphthalene with propylene was carried out under the same conditions as Example 9.

Test results of the alkylations of Example 9 and Comparative Example 8 are shown in TABLE 4.

TABLE 4

|  | Ex. 9 | Comp. Ex. 8 |
|---|---|---|
| Catalyst | Cat. 1 F (4.3) $SiO_2.Al_2O_3$ | $SiO_2.Al_2O_3$ |
| Conditions |  |  |
| LHSV ($Hr^{-1}$) | 4.8 | 4.8 |
| Temp. (°C.) | 280 | 280 |
| Pressure ($kg/cm^2G$) | 7.0 | 7.0 |
| Results (molar %) |  |  |
| naphthalene | 1.9 | 1.3 |
| MIPN | 19.4 | 21.3 |
| DIPN | 54.4 | 50.0 |
| (2,6DIPN) | (20.4) | (19.0) |
| TIPN | 22.5 | 23.9 |
| TetraIPN | 1.8 | 3.5 |

MIPN: monoisopropylnaphthalenes.
DIPN: diisopropylnaphthalenes containing 2,6-diisopropylnaphthalene
(2,6DIPN): 2,6-diisopropylnaphthalene
TIPN: triisopropylnaphthalenes
TetraIPN: tetraisopropylnaphthalenes

EXAMPLE 10

Alkylation of alpha-isopropylnaphthalene with propylene was carried out using the Catalyst 1 (silica-alumina catalyst containing 4.3 weight percent of fluorine) in the same manner as Example 1 under conditions described in TABLE 5.

COMPARATIVE EXAMPLE 9

The same silica-alumina used in Comparative Example 8 was used as the catalyst and the alkylation of alpha-isopropylnaphthalene with propylene was carried out under the same conditions as in Example 10.

Test results of the alkylations of Example 10 and Comparative Example 9 are shown in TABLE 5.

Example 10 shows that the transalkylation activity of the catalyst 1 according to the present invention is excellent compared to the silica-alumina catalyst used in Comparative Example 9.

TABLE 4

|  | Ex. 10 | Comp. Ex. 9 |
|---|---|---|
| Catalyst | Cat. 1 F (4.3) $SiO_2.Al_2O_3$ | $SiO_2.Al_2O_3$ |
| Conditions |  |  |
| LHSV ($Hr^{-1}$) | 4.8 | 4.8 |
| Temp. (°C.) | 280 | 280 |
| Pressure ($kg/cm^2G$) | 7.0 | 7.0 |
| Results (molar %) |  |  |
| naphthalene | 2.0 | 1.7 |
| MIPN | 19.9 | 21.0 |
| (alpha-MIPN) | (0.6) | (2.3) |
| (beta-MIPN) | (19.3) | (18.7) |
| DIPN | 54.0 | 49.8 |
| (2,6DIPN) | (20.2) | (18.9) |
| TIPN | 22.5 | 23.9 |
| TetraIPN | 1.6 | 3.6 |

MIPN: monoisopropylnaphthalenes.
DIPN: diisopropylnaphthalenes containing 2,6-diisopropylnaphthalene
(2,6DIPN): 2,6-diisopropylnaphthalene
TIPN: triisopropylnaphthalenes
TetraIPN: tetraisopropylnaphthalenes

EXAMPLE 11

(Catalyst life test)

400 cc of above-mentioned Catalyst 1 (silica-alumina containing 4.3 weight percent of fluorine) were filled in a test reactor and a long time life test of the catalyst was carried out by supplying naphthalene and two-fold molar quantity of propylene to the naphahalene under conditions of LHSV 1.0 Hr$^{-1}$ and a pressure of 7.0 kg/cm$^2$G. Temperature was gradually increased from 255° C. to 300° C. in steps. As the result, the yield of 2,6-diisopropylnaphthalene was dropped to less than 13 molar percent after 3,100 hours from the beginning of the reaction.

COMPARATIVE EXAMPLE 10

(Catalyst life test)

Using the same type of silica-alumina catalyst as used in Comparative Example 1, a long time life test of the catalyst was carried out in the same manner as Example 11.

As the result, the yield of 2,6-diisopropylnaphthalene was dropped to less than 13 molar percent after 2,700 hours from the beginning of the reaction.

I claim:

1. A method for preparation of 2,6-dialkylnaphthalene comprising: reacting naphthalene monoalkylnaphthalene or mixtures thereof having an alkyl group of 1 to 4 carbon atom(s) with an olefin having 2 to 4 carbon atoms, in the presence of a silica-alumina catalyst containing 0.1-15 weight percent of fluorine, under conditions of molar ratio of the olefin to the naphthalene the monoalkylnaphthalene or mixtures thereof of 0.5-3, a reaction temperature of 200°-450° C., a reaction pressure of 2-30 kg/cm$^2$G and a LHSV of 0.2-10 Hr$^{-1}$.

2. A method for preparation of 2,6-dialkylnaphthalene comprising:
    reacting naphthalene monoalkylnaphthalene or mixtures thereof having an alkyl group of 1 to 4 carbon atom(s) with an olefin having 2 to 4 carbon atoms, in the presence of a silica-alumina catalyst containing 0.5-13 weight percent of fluorine, under conditions of molar ratio of the olefin to the naphthalene monoalkylnaphthalene or mixtures thereof of 0.5-3, a reaction temperature of 220°-350° C., a reaction pressure of 3-15 kg/cm$^2$G and a LHSV of 0.2-5 Hr$^{-1}$.

3. A method for preparation of 2,6-dialkylnaphthalene comprising the following steps:
    supply naphthalene monoalkylnaphthalene or mixtures thereof having an alkyl group of 1 to 4 carbon atom(s) with an olefin having 2 to 4 carbon atoms to a reactor packed with a silica-alumina catalyst containing 0.1-15 weight percent of fluorine and reacting the olefin with the naphthalene and/or the monoalkylnaphthalene under conditions of molar ratio of the olefin to the naphthalene monoalkylnaphthalene or mixtures thereof of 0.5-3, a reaction temperature of 200°-450° C., a reaction pressure of 2-30 kg/cm$^2$G and a LHSV of 0.2-10 Hr$^{-1}$;
    separating and recovering 2,6-dialkylnaphthalene from the reaction product; and
    recycling the rest of the reaction product after the separation of dialkylnaphthalene(s) to said reactor.

4. A method for preparation of 2,6-dialkylnaphthalene comprising the following steps:
    supply naphthalene monoalkylnaphthalene or mixtures thereof having an alkyl group of 1 to 4 carbon atom(s) with an olefin having 2 to 4 carbon atoms to a reactor packed with a silica-alumina catalyst containing 0.5-13 weight percent of fluorine and reacting the olefin with the naphthalene and/or the monoalkylnaphthalene under conditions of molar ratio of the olefin to the naphthalene monoalkylnaphthalene or mixtures thereof of 0.5-3, a reaction temperature of 220°-350° C., a reaction pressure of 3-15 kg/cm$^2$G and a LHSV of 0.2-5 Hr$^{-1}$;
    separating and recovering 2,6-dialkylnaphthalene from the reaction product; and
    recycling the rest of the reaction product after the separation of 2,6-dialkylnaphthalene to said reactor.

* * * * *